United States Patent
Jeter et al.

(10) Patent No.: US 8,597,245 B2
(45) Date of Patent: Dec. 3, 2013

(54) MEDICAL INJECTOR WITH COUPLED BODY PORTIONS

(75) Inventors: Ruane S. Jeter, Los Angeles, CA (US); Richard A. Cronenberg, Mahwah, NJ (US); Lionel Vedrine, Palo Alto, CA (US); Atul Patel, Wilkes-Barre, PA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 92 days.

(21) Appl. No.: 13/063,806

(22) PCT Filed: Sep. 18, 2009

(86) PCT No.: PCT/US2009/057446
§ 371 (c)(1), (2), (4) Date: May 3, 2011

(87) PCT Pub. No.: WO2010/033782
PCT Pub. Date: Mar. 25, 2010

(65) Prior Publication Data
US 2011/0202013 A1    Aug. 18, 2011

Related U.S. Application Data

(60) Provisional application No. 61/192,465, filed on Sep. 18, 2008.

(51) Int. Cl.
*A61M 5/00* (2006.01)
*A61M 5/32* (2006.01)
*A61M 5/20* (2006.01)

(52) U.S. Cl.
USPC ............ 604/135; 604/194; 604/192; 604/187

(58) Field of Classification Search
USPC ......... 604/228, 223, 233, 181, 183–185, 194, 604/218, 135; 206/364
See application file for complete search history.

(56) References Cited

U.S. PATENT DOCUMENTS

| | | | | |
|---|---|---|---|---|
| 4,011,868 A | * | 3/1977 | Friend | 604/194 |
| 5,336,201 A | * | 8/1994 | von der Decken | 604/223 |
| 5,830,194 A | * | 11/1998 | Anwar et al. | 604/223 |
| 6,752,788 B2 | | 6/2004 | Tuen | |

(Continued)

FOREIGN PATENT DOCUMENTS

| EP | 2364741 A1 | * | 9/2011 |
|---|---|---|---|
| WO | WO 2004/098687 | * | 11/2004 |

*Primary Examiner* — Emily Schmidt
*Assistant Examiner* — Matthew A Engel
(74) *Attorney, Agent, or Firm* — Hoffmann & Baron, LLP

(57) ABSTRACT

A medical injector is provided herein which includes first and second body portions each having a longitudinal axis and configured to couple at a coupling. The first and second body portions are complementarily formed so as to be movable about the coupling. The medical injector also includes an axially-displaceable plunger; biasing element for advancing the plunger a predetermined distance; and, a releasable retainer for releasably retaining the plunger in a first state against the force of the biasing element. In an initial state, the axes of the first and second body portions are not aligned and the plunger is in the first state. In a coupled state, the axes of the first and second body portions are axially aligned, and the releasable retainer releases the plunger, thereby allowing the biasing element to advance the plunger the predetermined distance. Advantageously, the subject invention provides a medical injector having an automated plunger drive which is triggered upon assembly of the pen injector, thereby minimizing premature or failed activations.

3 Claims, 12 Drawing Sheets

(56) References Cited

U.S. PATENT DOCUMENTS

| | | |
|---|---|---|
| 2002/0068907 A1 | 6/2002 | Dysarz |
| 2003/0149403 A1 | 8/2003 | Barker et al. |
| 2004/0215154 A1 | 10/2004 | Hwang et al. |
| 2006/0052748 A1 | 3/2006 | Coelho et al. |
| 2007/0106224 A1 | 5/2007 | Hwang |
| 2008/0208138 A1 | 8/2008 | Lim et al. |

* cited by examiner

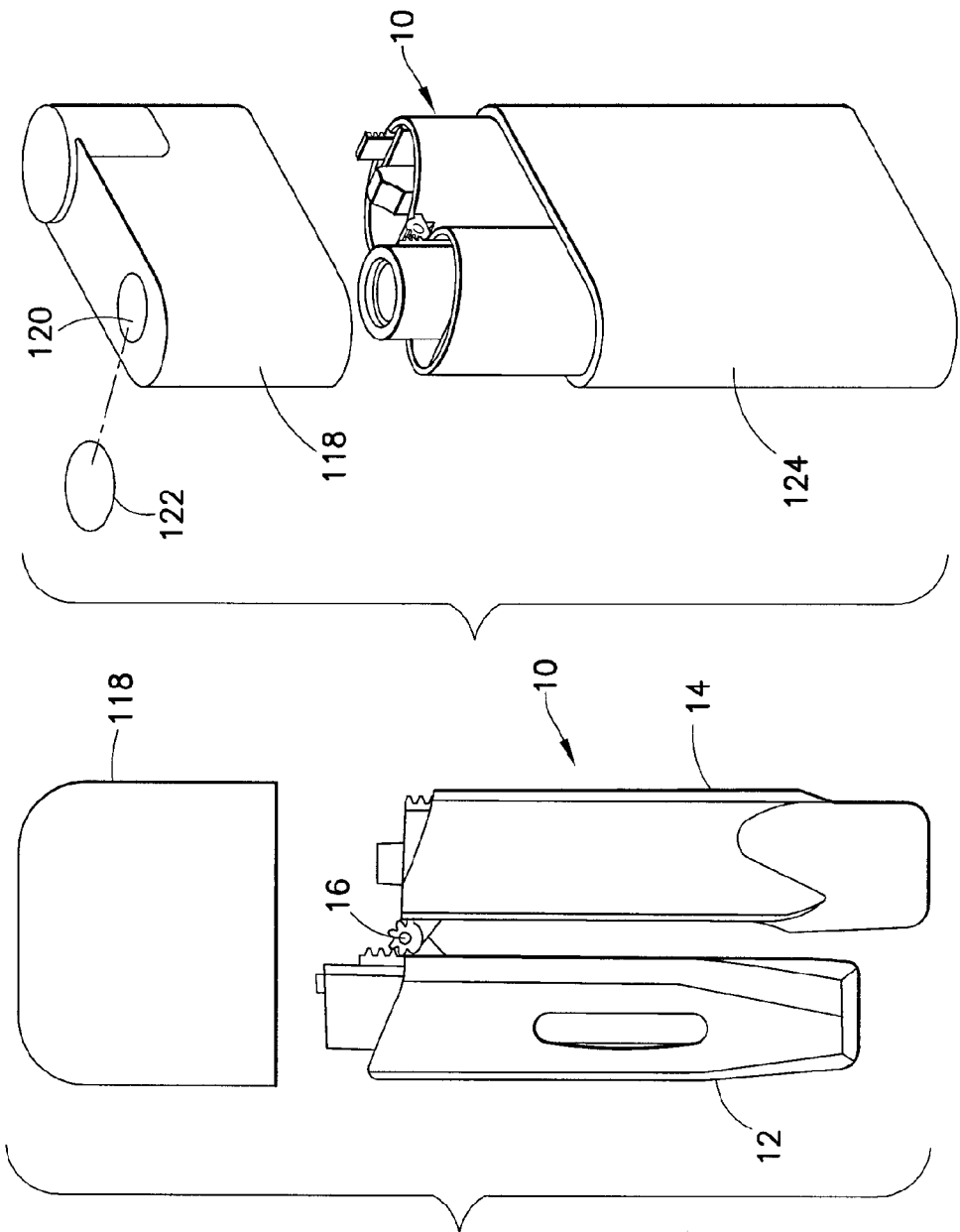

US 8,597,245 B2

MEDICAL INJECTOR WITH COUPLED BODY PORTIONS

FIELD OF THE INVENTION

This invention relates to medical injectors, and, more particularly, to medical injectors having plunger drive mechanisms.

BACKGROUND OF THE INVENTION

Medical injectors are well known in the prior art, including injectors which have internal drive mechanisms for plunger advancement. Plunger advancement may be utilized to conduct automated reconstitution of a two-or more part medicament and/or to cause automated injection. More specifically, the automation of plunger advancement may be utilized to cause combination of a multiple part (e.g., wet/dry) medicament. In addition, or alternatively, the automated advancement of the plunger may cause a needle to be advanced for injection and/or medicament to be driven through the needle during injection. Such automated action requires a trigger mechanism. Concerns exist over premature or failed trigger activation.

SUMMARY OF THE INVENTION

A medical injector is provided herein which includes first and second body portions each having a longitudinal axis and configured to couple at a coupling. The first and second body portions are complementarily formed so as to be movable about the coupling. The medical injector also includes an axially-displaceable plunger; biasing element for advancing the plunger a predetermined distance; and, a releasable retainer for releasably retaining the plunger in a first state against the force of the biasing element. In an initial state, the axes of the first and second body portions are not aligned and the plunger is in the first state. In a coupled state, the axes of the first and second body portions are axially aligned, and the releasable retainer releases the plunger, thereby allowing the biasing element to advance the plunger the predetermined distance. Advantageously, the subject invention provides a medical injector having an automated plunger drive which is triggered upon assembly of the pen injector, thereby minimizing premature or failed activations.

These and other features of the subject invention will be better understood through a study of the following detailed description and accompanying drawings.

BRIEF DESCRIPTION OF THE DRAWINGS

FIGS. 17-20 show cap configurations useable with the subject invention.

DETAILED DESCRIPTION OF THE INVENTION

Figure 1:
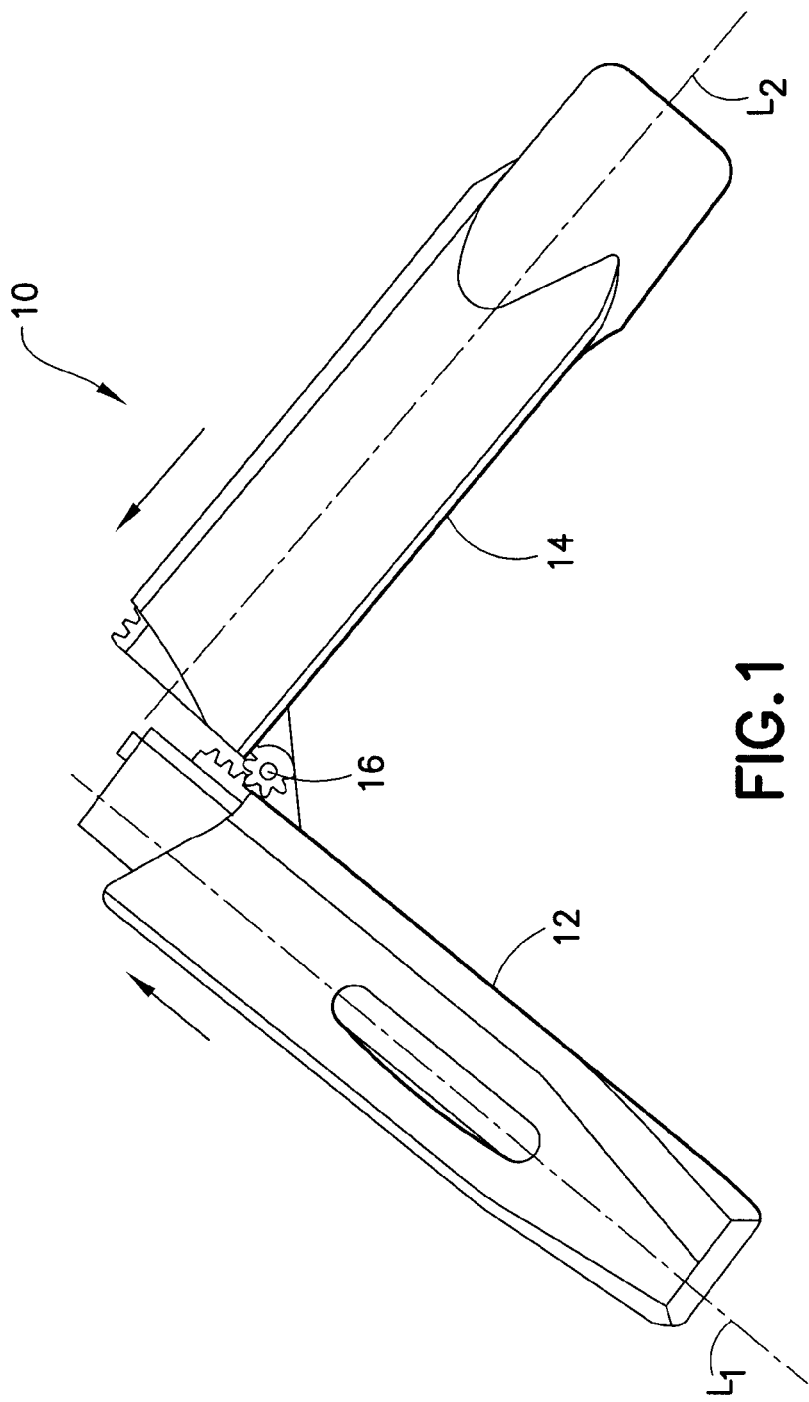
FIGS. 1 and 2 show a medical injector formed in accordance with the subject in pre-assembled and assembled states, respectively.

With reference to the figures, a medical injector is shown and generally designated with the reference numeral 10. The medical injector 10 may be of various types, but preferably is of the pen injector type. The medical injector 10 may be used to administer various injectable liquids, particularly medicaments.

Figure 2:
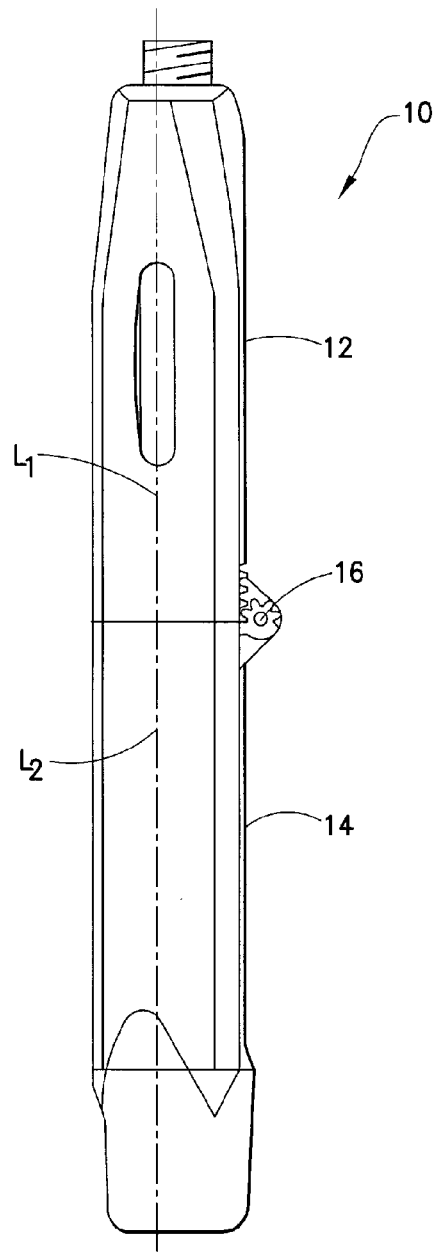

With reference to FIG. 1, the medical injector 10 includes first and second body portions 12, 14 which are connected through a movement relative to coupling 16. Preferably, the coupling 16 is a hinged connection. The first and second body portions 12, 14 are complementarily formed so as to be assembled together with sufficient movement, e.g., rotation, about the coupling 16. As shown in FIG. 1, longitudinal axes L1, L2 of the first and second body portions 12, 14 are not axially (not collinearly) aligned in an initial state of the medical injector 10. The assembled state of the medical injector 10 is shown in FIG. 2 where the longitudinal axes L1, L2 are axially aligned.

Figure 3:
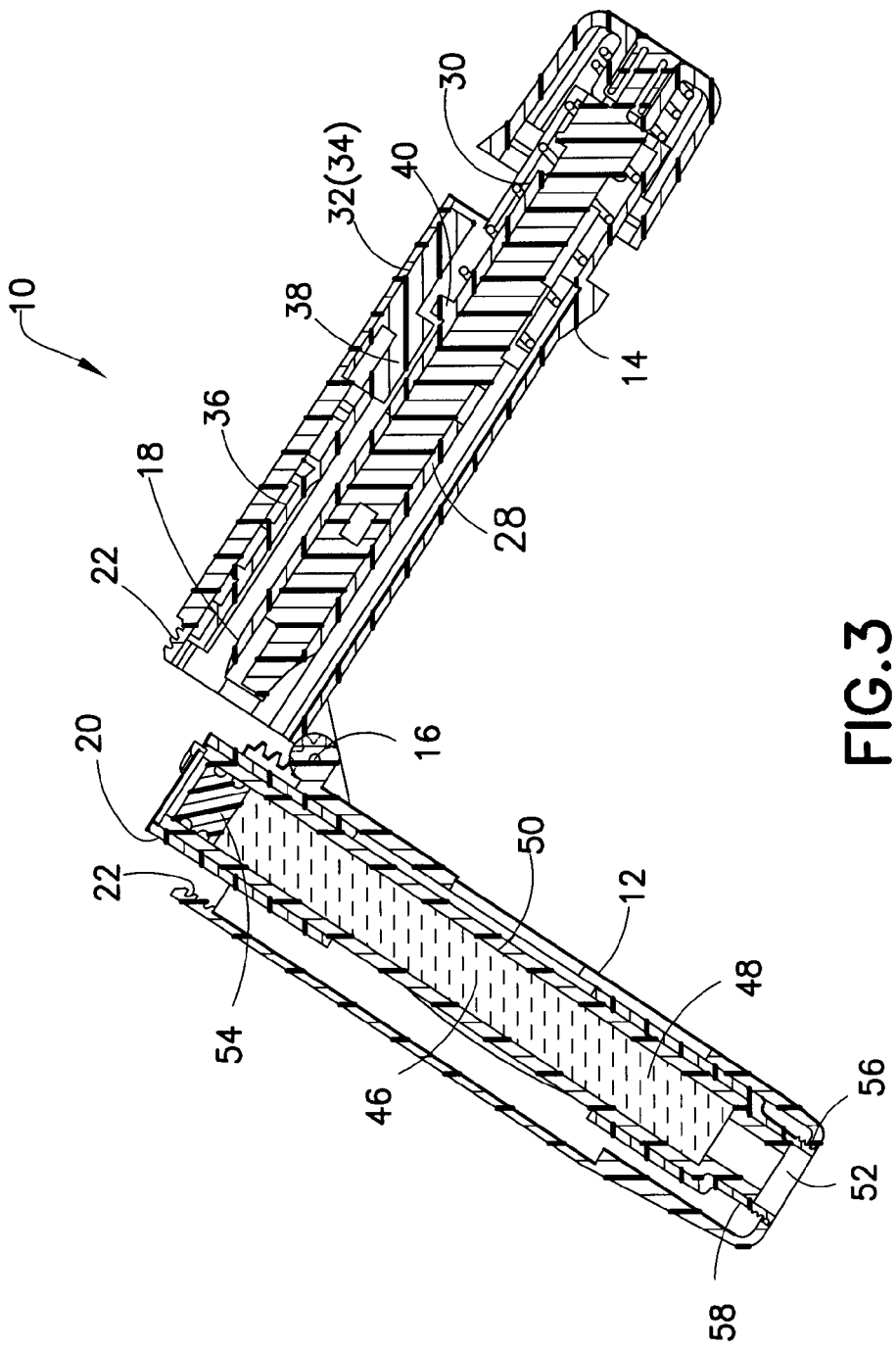

The first and second body portions 12, 14 are preferably formed of rigid material and to varying extents accommodate different portions of the medical injector 10. Preferably, to facilitate assembly, as shown in FIG. 3, a reduced diameter portion 18 is formed on one of the first and second body portions 12, 14 with a corresponding telescoping portion 20 being formed on the other of the first and second body portions 12, 14. In this manner, the first and second body portions 12, 14 may be assembled with the telescoping portion 20 being disposed over the reduced diameter portion 18. In addition, cooperating locking elements 22, such as cooperating detent and groove, meshing teeth, and/or other snap-together locking features, may be provided to lock the first and second body portions 12, 14 together once assembled.

Figure 7:
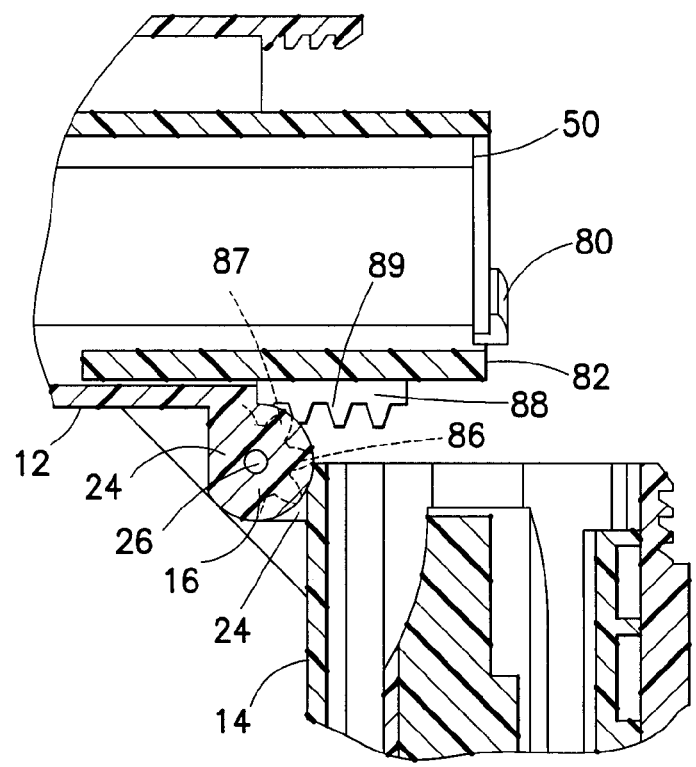
FIGS. 7 and 8 show an arrangement for achieving relative movement of components.
Figure 8:
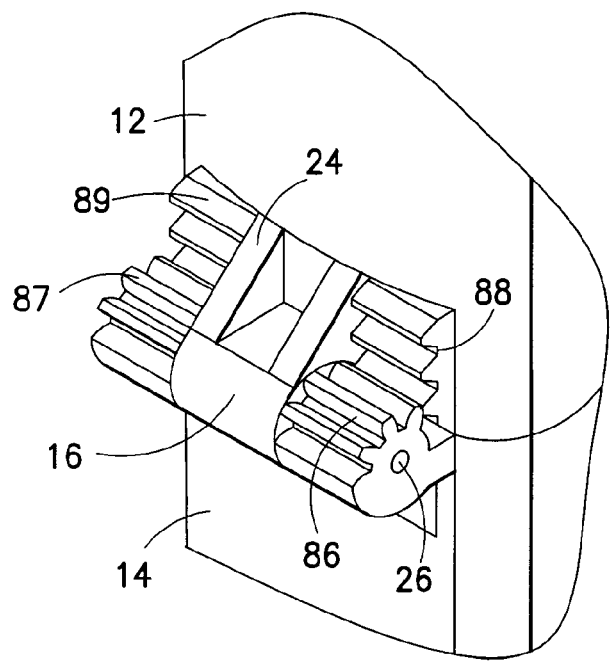

As shown in the figures, particularly FIGS. 7 and 8, the coupling 16 may be a pin hinge where brackets 24 are provided on the first and second body portions 12, 14 which are joined together to rotate about a central pin 26. As will be appreciated by those skilled in the art, a living hinge may also be used for the coupling 16. The coupling 16 is positioned and formed to allow proper movement, e.g., rotation, thereabout in allowing the first and second body portions 12, 14 to come together and form the medical injector 10.

The medical injector 10 includes an axially-displaceable plunger 28. The plunger 28 may be formed as a single piece or by modular components. The modular components may be fixed to one another or located adjacently, but not connected, so as to move together. In a preferred embodiment, the plunger 28 is initially located in the second body portion 14. A biasing element 30 is also provided configured and positioned to advance the plunger 28 a predetermined distance. Preferably, the biasing element 30 is a compression or coil spring, but other biasing elements may likewise be utilized. Preferably, the biasing element 30 is positioned in the second body portion 14.

A releasable retainer 32 is provided configured and positioned to releasably retain the plunger 28 in an initial first state against the force of the biasing element 30. The releasable retainer 32 is configured such that, upon assembly of the first and second body portions 12, 14, the releasable retainer 32 releases the plunger 28 thereby allowing the biasing element 30 to advance the plunger 28 the predetermined distance. As will be appreciated by those skilled in the art, various releasable retainers may be used with the subject invention.

It is preferred that the plunger 28 be advanced in a distal direction. As used herein, distal refers to a direction towards a patient during use, while proximal refers to a direction away from a patient during use.

Figure 4:
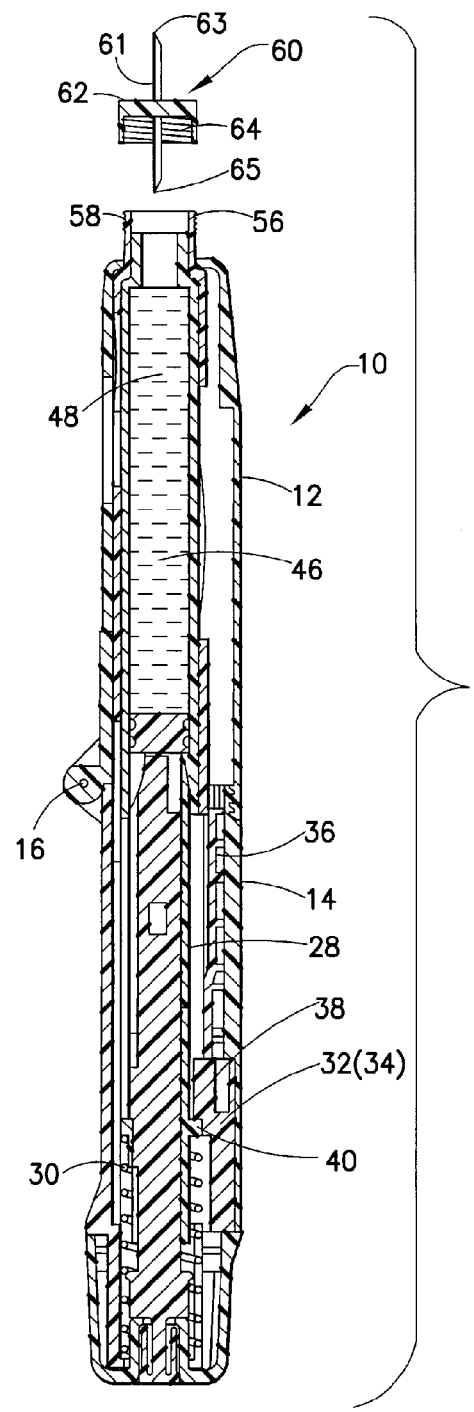
FIGS. 3 and 4 are cross-sectional views of a medical injector formed in accordance with the subject invention.
Figure 5:
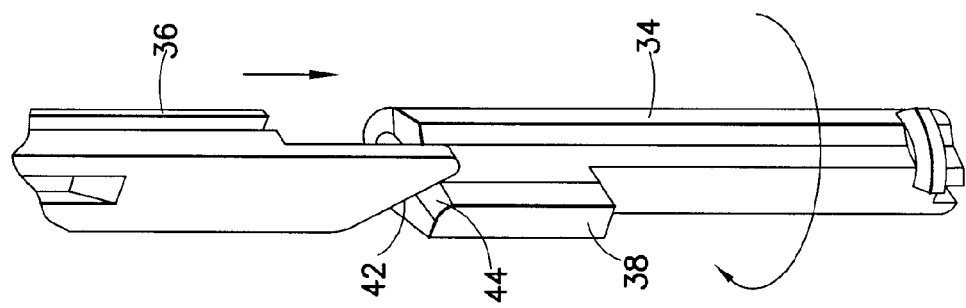
FIG. 5 is a schematic of a releasable retainer useable with the subject invention.

By way of non-limiting example, the releasable retainer 32 may be a displaceable cam member 34, as shown in FIGS. 3-5. As shown in FIGS. 3 and 4, upon assembly of the first and second body portions 12, 14, a cam arm 36 may be displaced, such as by interfering engagement with a portion or component of the first body portion 12, thus causing displacement of the cam member 34. The cam member 34 may include a protruding stop member 38 formed to interferingly engage a portion of the plunger 28, such as shoulder 40, in causing retention thereof in an initial, first state, before use. With displacement of the cam member 34, the cam member 34 releases the shoulder 40 thus allowing the biasing element 30 to drive the plunger 28 distally. It is preferred that the cam member 34 be pivotally connected to the second body portion 14, so as to be rotatable relative thereto. Displacement of the cam member 34 may be achieved by interengagement of ramped surface 42 of the cam arm 36 acting against engagement surface 44 of the cam member 34 under movement of the cam arm 36 resulting in sufficient rotation of the cam member 34 to clear the stop member 38 from the shoulder 40.

The medical injector 10 includes a reservoir 46 disposed in the first body portion 12 formed to accommodate medicament or other substance 48 for injection into a patient. As shown in FIG. 3, the reservoir 46 may be a single chamber disposed in a barrel 50 sealed at a proximal end by a septum 52 and sealed at a distal end by a stopper 54 which is formed to be slidable through the barrel 50 for urging the substance 48 therefrom, as known in the art. The medical injector 10 also includes a needle mounting surface 56 having features 58 formed thereon for mounting a needle 60 thereto. The needle 60 may include a hub 62 having mounting features 64 provided thereon for cooperative engagement with the features 58 in mounting the needle 60 to the needle mounting surface 56. The features 58 and the mounting features 64 may be of any known cooperating elements which permit a mechanical connection therebetween, such as threads or bayonet lock, and/or a frictional interengagement, such as a Luer mounting. The needle mounting surface 56 may be formed on the first body portion 12 or a component thereof.

The needle 60 also includes a needle cannula 61 having a distal end 63, formed for insertion into a patient, and a proximal end 65.

Figure 6:
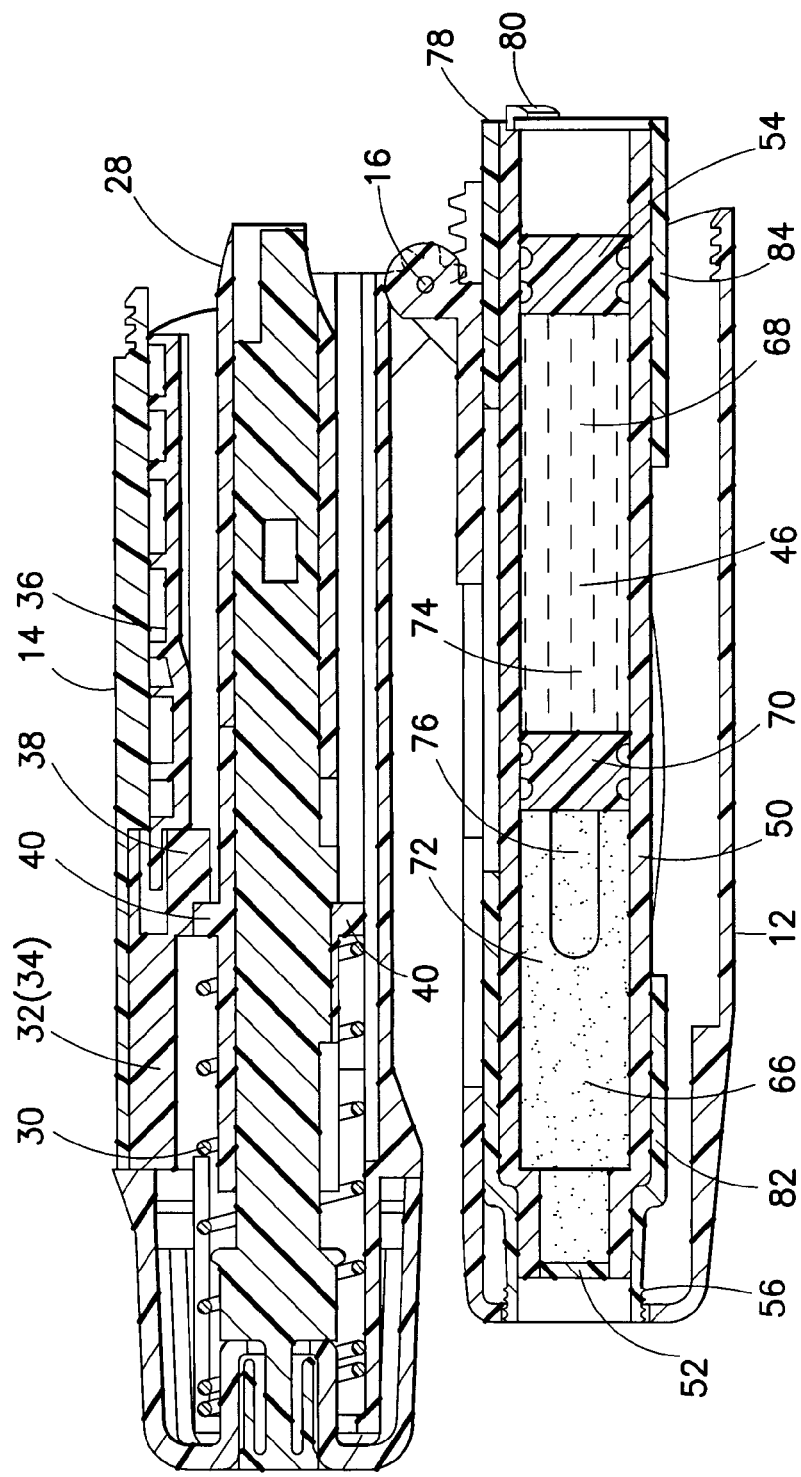
FIG. 6 is a cross-sectional view of a medical injector formed in accordance with the subject invention having a reservoir configured for reconstitution.

The reservoir 46 may be configured to accommodate multiple components which are mixable for reconstitution. For example, as shown in FIG. 6, the reservoir may accommodate first and second mixable components 66, 68. The stopper 54 may be associated with the reservoir 46 such that distal advancement of the stopper 54 over a predetermined distance shall cause mixing of the first and second mixable components 66, 68. Any known arrangement for allowing such mixing may be utilized. By way of non-limiting example, the first and second mixable components 66, 68 may be separated by a secondary stopper 70. The secondary stopper 70 divides the reservoir 46 into first and second chambers 72, 74, respectively, accommodating the first and second mixable components 66, 68. The septum 52 seals off the distal end of the first chamber 72, while the stopper 54 is positioned to seal off the proximal end of the second chamber 74. Preferably, if a dry component is used as one of the mixable components, the dry mixable component is located in the first chamber 72.

One or more by-pass channels 76 are formed in the wall of the reservoir 46. In an initial state, as shown in FIG. 6, the secondary stopper 70 is located at least partially proximally of the by-pass channels 76 so as to define a seal between the first and second chambers 72, 74 and to define a seal between the second chamber 74 and the by-pass channels 76. With distal advancement of the stopper 54, and with the second mixable component 68 being wet and generally incompressible, force of movement of the stopper 54 is transmitted to the secondary stopper 70 through the second mixable component 68. With sufficient distal movement of the secondary stopper 70, the second chamber 74 comes into communication with the by-pass channels 76, thus allowing the second mixable component 68 to be urged into the first chamber 72 with further distal movement of the stopper 54. With sufficient distal advancement of the stopper 54, the second chamber 74 is collapsed with none or substantially none of the second mixable component 68 remaining therein. In addition, the secondary stopper 70 is located so as to define a seal between the first chamber 72 and the by-pass channels 76. The first and second mixable components 66, 68 are mixed within the first chamber 72, such as through agitation of the medical injector 10, so as to produce the injectable substance 48, ready for injection.

The barrel 50 of the reservoir 46 may be the barrel of a separate drug cartridge, as shown in the figures, or a portion of the medical injector 10, particularly the first body portion 12.

As will be recognized by those skilled in the art, other arrangements for permitting reconstitution may be utilized. In addition, more than two-part systems, such as three-part and so forth, systems may be utilized. Active medical ingredients may be included in one or both of the first and second mixable components 66, 68. The first mixable component 66 may be dry (e.g., a powder or granular substance) and/or a liquid (e.g., flowable (slurry or liquid)). As mentioned above, the second mixable component 70 is preferably only a wet flowable component, such as a liquid or slurry.

Distal advancement of the plunger 28 under force of the biasing element 30 may be used to achieve one or more objectives. The plunger 28 is configured to act against the stopper 54 and cause displacement thereof. With the reservoir 46 being configured for reconstitution, autoreconstitution of the contents of the reservoir 46 may be achieved. In addition, or alternatively, the medical injector 10 may be configured to be an autoinjector, where the needle 60 is initially housed within the first body portion 12 and forced thereout of under force of the biasing element 30 so as to pierce a patient's skin, e.g., with forward movement of the reservoir 46, as known in the art. In addition, or alternatively, distal advancement of the plunger 28 may cause administration of the contents of the reservoir 46 through the injected needle.

Depending on the desired effect, the medical injector 10 may be configured to have the plunger 28 be driven a predetermined distance. A physical stop, such as interengagement between the shoulder 40 and a proximal end 78 of the reservoir 46 (e.g., proximal end of the barrel 50), may be employed to limit distal advancement of the plunger 28. Under certain circumstances, the plunger 28 may be distally advanced without the needle 60 being mounted to the medical injector 10. Thus, the reservoir 46 is not vented during such action. With the needle 60 being subsequently mounted to the reservoir 46, any residual gases trapped in the reservoir 46 are purged through the needle 60. It may be preferred to not provide a physical stop to the distal advancement of the plunger 28. In this manner, the contents of the reservoir 46 may be maximally compressed under force of the biasing element 30. With subsequent mounting of the needle 60 onto the medical injector 10, the reservoir 46 is vented thus permitting further distal advancement of the plunger 28. This secondary distal advancement may assist in priming the needle 60 for use.

FIG. 6 shows the medical injector 10 in a state prior to use. As shown therein, the reservoir 46 may be a drug cartridge which is separable from the first body portion 12. One or more cartridge retaining hooks 80 may be provided to act against the barrel 50 in holding the barrel 50 in the first body portion 12. It is preferred that the cartridge retaining hooks 80 be resilient so as to permit outward deflection in loading the reservoir 46 into the first body portion 12.

It is preferred that a cartridge retaining element 82 be provided which includes a sleeve 84 into which the reservoir 46 is disposed. In addition, it is preferred that the needle mounting surface 56 and the cartridge retaining hooks 80 be formed on the cartridge retaining element 82. The cartridge retaining element 82 may be retained in the first body portion 12 through any known fixing arrangement, such as a mechanical connection, e.g., snap engagement or frictional connections, and/or chemical or adhesive connections, such as fusion, welding or gluing.

Movement of one or more of the components relative to the first and/or second body portions 12, 14 may be desired. To obtain such relative movement, with reference to FIGS. 7 and 8, a pinion 86 may be mounted to one of the first and second body portions 12, 14 with a corresponding rack 88 being mounted to the component intended for relative movement. As shown in the Figures, the cartridge retaining element 82 may be configured for movement relative to the first body portion 12. To this end, the cartridge retaining element 82 may be nested within the first body portion 12 with the rack 88 being located thereon. The pinion 86 and the rack 88 are formed with teeth 87, 89 formed for cooperating meshing engagement. With movement about the coupling 16, the pinion 86 rotates and causes linear translation of the rack 88, thus causing the cartridge retaining element 82 to translate relative to the first body portion 12. This linear translation permits for various axial adjustments of the reservoir 46, or other components. The needle mounting surface 56 may be formed on the cartridge retaining element 82 and caused to be initially hidden in the first body portion 12 (FIG. 1) with subsequent distal advancement through translation of the cartridge retaining element 82 causing the needle mounting surface 56 to become exposed (FIG. 2). In this manner, control can be established over proper timing of the needle mounting surface 56 during sequence of preparation of the medical injector 10. In particular, it may be desired to expose the needle mounting surface 56 only after reconstituting, if reconstitution is utilized.

The medical injector 10 may be a fixed dose injector configured to administer single or multiple fixed doses. In addition, the medical injector 10 may be configured to permit dose setting for either a single or multiple doses. In a preferred embodiment, the medical injector 10 is a single, variable-dose autoreconstitution injector.

As will be appreciated by those skilled in the art, various configurations to permit dose setting may be utilized. By way of non-limiting example, and with reference to FIGS. 9 and 10, a knob stem 90 may be provided with a plurality of axially and radially spaced-apart abutment surfaces 92.

The abutment surfaces 92 are axially alignable with an engagement surface 94 formed on the plunger 28 such that with sufficient distal displacement of the knob stem 90 at least one of the abutment surfaces 92 will be caused to engage the engagement surface 94 and transmit force of movement to the plunger 28. In this manner, distal displacement of the knob stem 90 may be transmitted to the plunger 28. Moreover, stroke length corresponding to the movement of the plunger 28 may be adjusted depending on the abutment surface 92 which is in engagement with the engagement surface 94. The greater the initial distance of the abutment surfaces 92 from the engagement surface 94, the corresponding smaller dose that will be caused to be administered. Regardless of the selected dose amount, it is preferred that the knob stem 90 having a fixed length of stroke for distal displacement during administration of an injection. The further abutment surfaces 92 have greater lost motion with distal movement of the knob stem 90 and, thus, less distance engaging the engagement surface 94. The extent of movement of the plunger 28 dictates the extent of movement of the stopper 54 and, thus, dictates the amount of the injectable solution 48 to be driven from the reservoir 46 in an injected dose.

Figure 9:
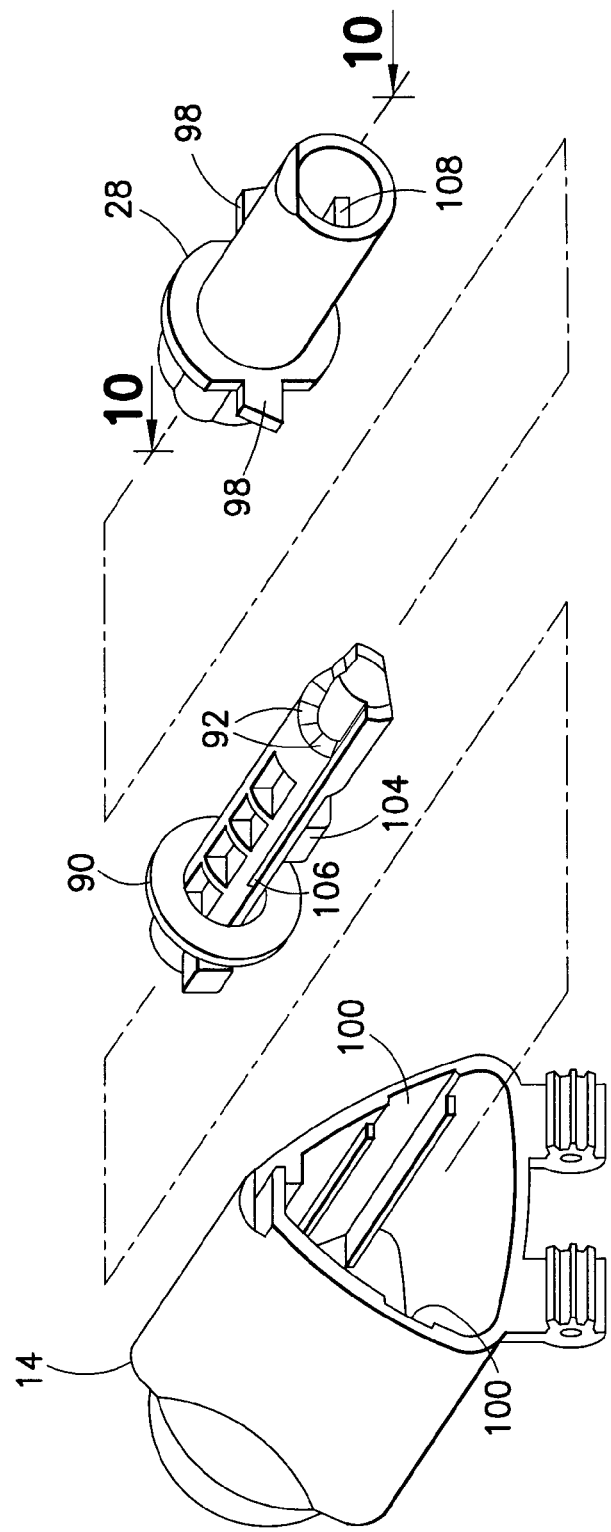
FIG. 9 is an exploded view of components useable with the subject invention.

The dose is selected by rotating a dose knob 96 which is fixed to the knob stem 90 so as to rotate therewith. The dose knob 96 and the knob stem 90 can be connected through any known manner, including through cooperating mechanical elements. To prevent the dose knob 96 from being inadvertently turned prior to proper preparation of the medical injector 10, such as prior to mixing of the mixable components 66, 68, assembly of the first and second body portions 12, 14, and so forth, the knob stem 90 may be coupled to the plunger 28 so as to prevent relative rotation therebetween with the plunger 28 being non-rotatably coupled to the second body portion 14. With reference to FIG. 9, the plunger 28 may have one or more lobes 98 formed to nest in corresponding channels 100 formed in the second body portion 14. The plunger 28 may slide along the channels 100 without rotating relative thereto. In turn, the plunger 28 may have one or more internal slots 102 in which are initially nested corresponding splines 104 protruding from the plunger 28. With distal advancement of the plunger 28, the plunger 28 may decouple from the knob stem 90 so as to permit relative rotation therebetween.

Figure 10:
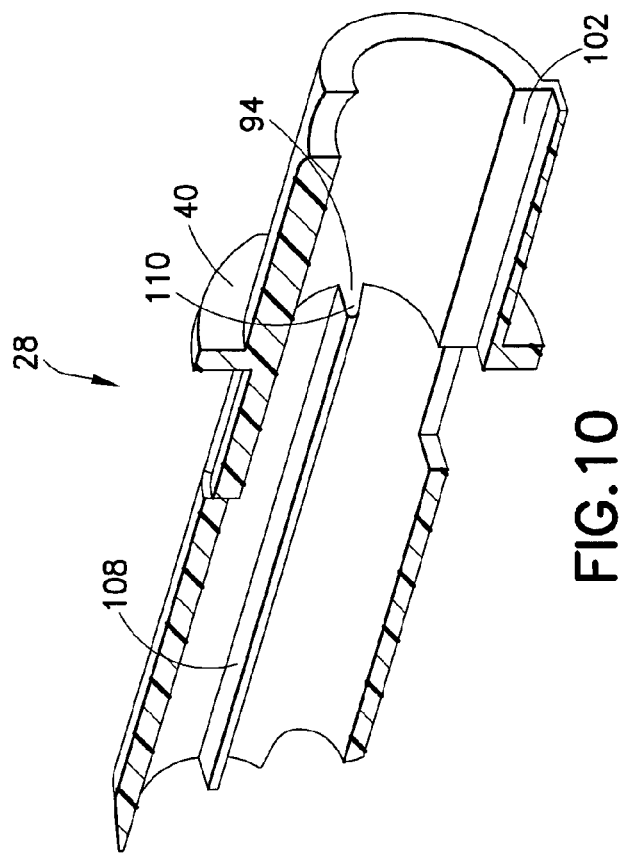
FIG. 10 is a cross-sectional view taken along line 10-10 of FIG. 9.

In addition, with reference to FIGS. 9 and 10, a groove 106 may be formed in the knob stem 90 corresponding to a rib 108 formed on the plunger 28. In an initial state, the rib 108 nests within the groove 106 so as to prevent relative rotation between the plunger 28 and the knob stem 90. With distal advancement of the plunger 28 being completed, such as with completed reconstitution, the plunger 28 may be advanced so as to have the rib 108 removed from the groove 106 and to have the spline 104 removed from the internal slot 102. The knob stem 90 is then free to rotate in setting a dose. Alternatively, the rib 108 may still be partially nested in the groove 106 even after distal advancement of the plunger 28, such as to a post-reconstituted state. With this configuration, the knob stem 90 may be proximally displaced to have the rib 108 removed from the groove 106 thus permitting subsequent dose setting. The dose is administered by causing distal advancement of the knob 90 once the dose has been properly set.

It is noted that the engagement surface 94 may be located at a proximal end 110 of the rib 108.

Figure 11:
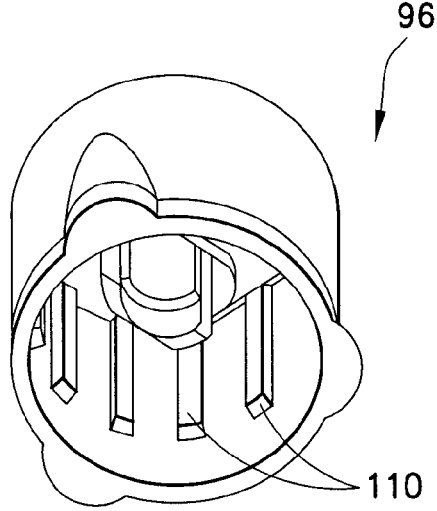
FIG. 11 is a perspective view of a dose knob useable with the subject invention.
Figure 12:
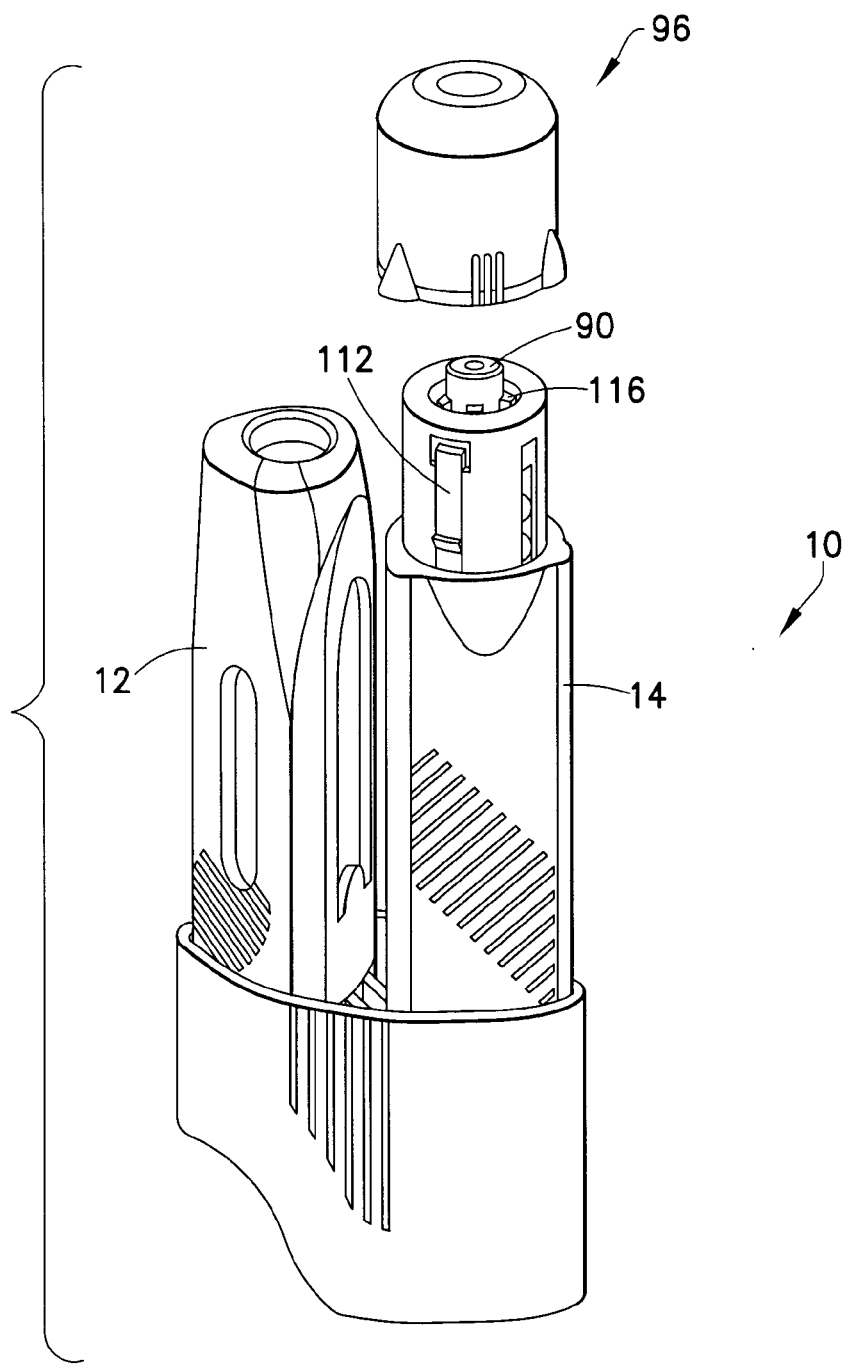
FIG. 12 is an exploded view of the subject invention.

It is preferred that the dose knob 96 be releasably retained in positions corresponding to the various dose settings. In this manner, it is preferred that once a dose has been set, there is no rotation of the dose knob 96 during distal displacement thereof, thus avoiding that an improper of the abutment surfaces 92 engage the engagement surface 94. Such an arrangement is disclosed in U.S. Pat. No. 6,793,646. As shown in U.S. Pat. No. 6,793,646, and with reference to FIGS. 11 and 12, one or more tabs 110 may be formed on the dose knob 96 which are selectively engageable with one or more positioning channels 112 formed on the second body portion 14. The positioning channels 112 may be circumferentially spaced apart and positioned to represent dose settings corresponding to the abutment surfaces 92. The tabs 110 nest in the positioning channels 112 at given radial positions of the dose knob 96 corresponding to different dose sizes. With turning of the dose knob 96, the tabs 110 are caused to by-pass the dose positioning channels 112. The positioning channels 112 maintain the radial position of the dose knob 96.

In addition, it is preferred that the dose knob 96 be limited in axial movement so as to permit a fixed stroke length of distal advancement for dose administration. The second body portion 14 may be provided with a reduced diameter opening 116 sized and positioned to interferingly engage the knob stem 90 upon a predetermined extent of proximal movement. The stroke of an injection is defined by the extent of proximal movement of the knob stem 90.

Figure 13:
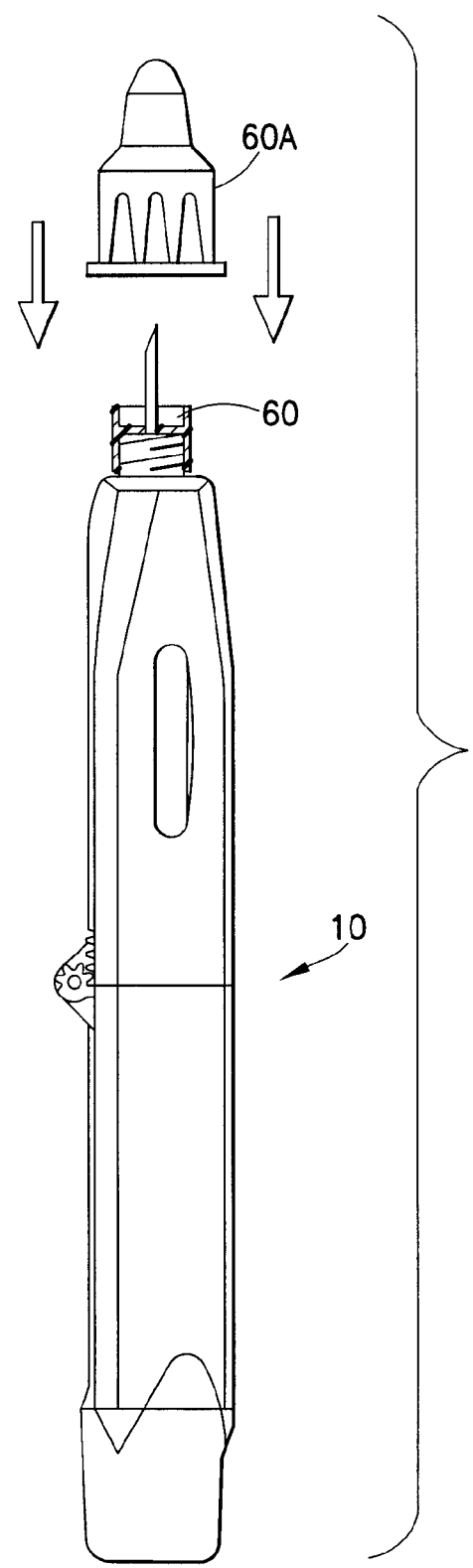
FIGS. 13-16 show operation of a medical injector formed in accordance with the subject invention.

For use, the medical injector 10 is initially presented in the state shown in FIG. 1, where the first and second body portions 12, 14 are separated. To prepare for use, the first and second body portions 12, 14 are moved about the coupling 16 so as to come to the assembled state shown in FIG. 2. It is preferred that no needle be mounted to the medical injector 10 prior to assembly. With assembly, the plunger 28 is caused to be distally advanced under force of movement by the biasing element 30. Reconstitution and/or other effects are achieved through this automated movement. Thereafter, the needle 60 is mounted to the medical injector 10 as shown in FIG. 13. The needle 60 may be provided with a cap or shield 60A. Any gases trapped in the reservoir 46 are purged through the needle 60 and the needle 60 may be primed for use.

Figure 14:
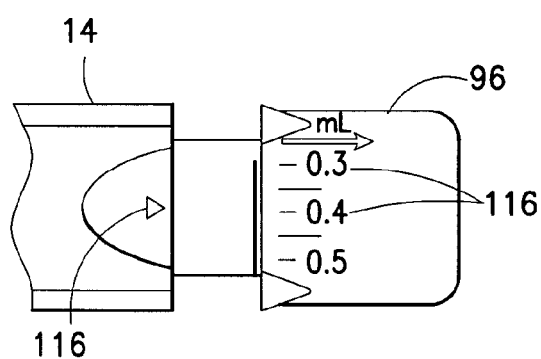
Figure 15:
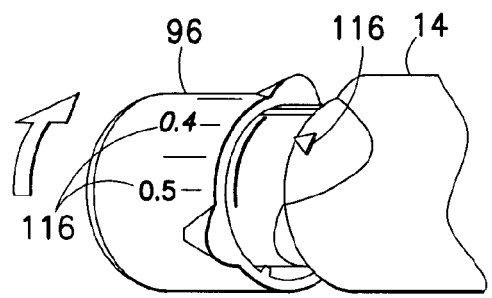
Figure 16:
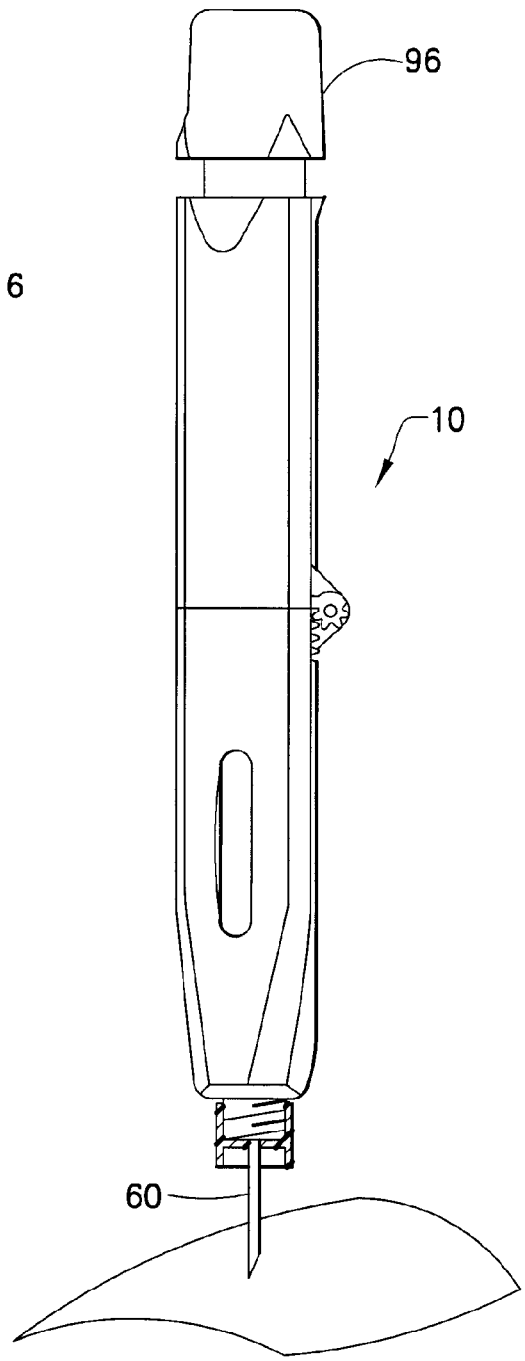
Figure 19:
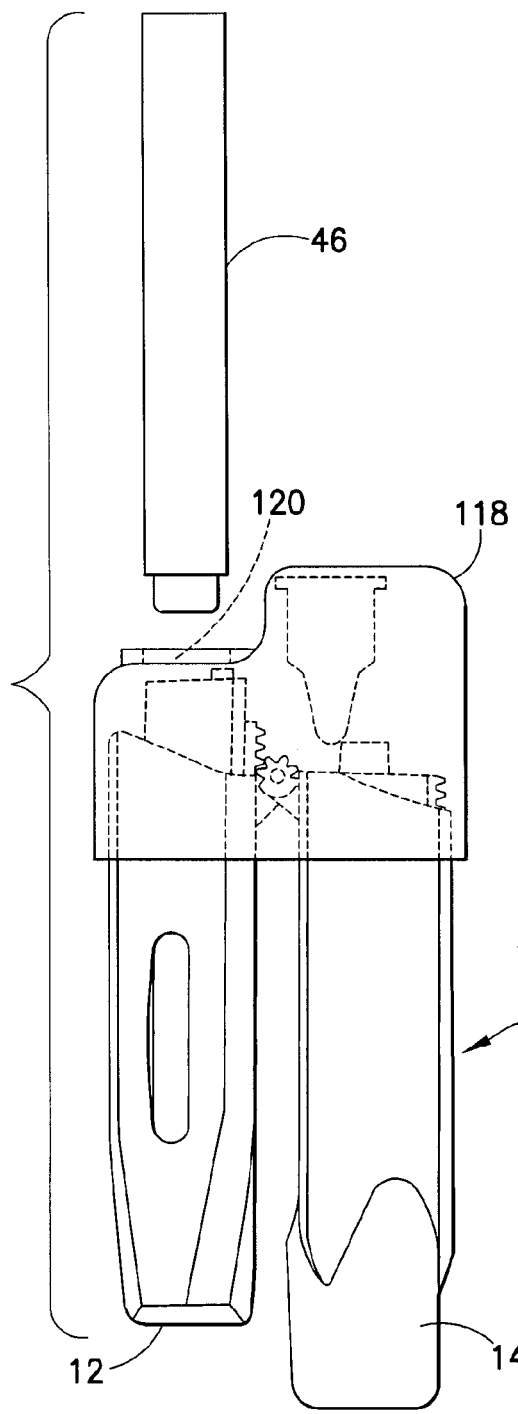
Figure 20:
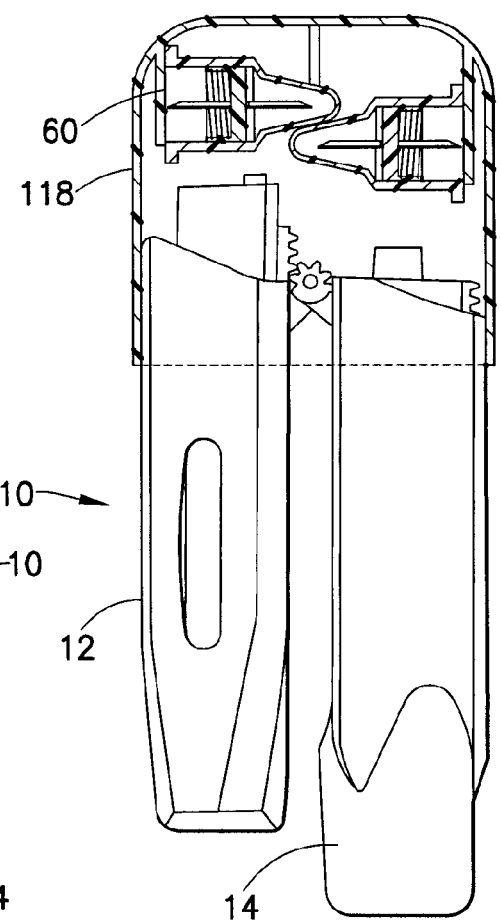

With reference to FIGS. 14 and 15, a dose may be selected by proximally withdrawing the dose knob 96. Proximal withdrawal of the dose knob 96 is limited, as described above. Once withdrawn, the dose knob 96 may be rotated to a desired setting. Indicia 116 may be provided to represent doses. The indicia 116 may include numeral representations and a pointer or other indicator. With reference to FIG. 16, the needle 60 is caused to pierce the skin of a patient and the dose knob 96 is then depressed to cause the knob stem 90 to advance distally. Interengagement between the selected of the abutment surfaces 92 and the engagement surface 94 causes the plunger 28 to drive the stopper 54 in administering an injection.

With the pre-use assembly of the medical injector 10, a cap 118 may be provided to cover at least partially the first and second body portions 12, 14, particularly about the coupling 16 as shown in FIGS. 17-20.

The cap 118 may be formed of a rigid material with a general cup shape. A loading aperture 120 may be formed in the cap 118 positioned over the first body portion 12 so as to allow the reservoir 46 to pass therethrough and be loaded into the first body portion 12. In this manner, a medical injector 10 may be stored without the reservoir 46 being located therein. The reservoir 46 may be loaded into the medical injector 10 without the cap 118 having to be removed therefrom. In addition, the cap 118 may be formed to accommodate one or more of the needles 60 therein. To maintain a clean and sterile environment within the cap 118, a sterility barrier 122, such as a removable film, is preferably provided to cover the loading aperture 120. The cap 118 may also be configured to form a tight seal about the medical injector 10. A complimentary compartment 124 may be provided with the cap 118 to wholly enclose the medical injector 10.

What is claimed is:

1. An injection device comprising:
   first and second body portions each having a longitudinal axis and configured to couple together at a coupling, said first and second body portions being complementarily formed so as to be movable about said coupling;
   an axially-displaceable plunger;
   a spring for advancing said plunger a predetermined distance; and
   a releasable retainer for releasably retaining said plunger in a first state against the force of said spring,
   wherein, in an initial state, said axes of said first and second body portions are not axially aligned and said plunger is in said first state, and
   wherein, in a coupled state, said axes of said first and second body portions are axially, and collinearly, aligned and said releasable retainer releases said plunger thereby allowing said spring to advance said plunger said predetermined distance.

2. An injection device as in claim 1, wherein said coupling is a hinged connection.

3. An injection device as in claim 2, wherein said first and second body portions are rotatable about said hinged connection.

* * * * *

UNITED STATES PATENT AND TRADEMARK OFFICE
CERTIFICATE OF CORRECTION

PATENT NO.        : 8,597,245 B2                                                        Page 1 of 1
APPLICATION NO. : 13/063806
DATED             : December 3, 2013
INVENTOR(S)      : Jeter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 138 days.

Signed and Sealed this
Twenty-second Day of September, 2015

Michelle K. Lee
*Director of the United States Patent and Trademark Office*